United States Patent [19]

Beaudet et al.

[11] Patent Number: 5,760,188
[45] Date of Patent: Jun. 2, 1998

[54] MARKER FOR NEUROTENSIN RECEPTOR

[75] Inventors: Alain Beaudet, Mount Royal; Marie-Pierre Faure, St-Laurent; Pierrette Gaudreau, Brossard, all of Canada

[73] Assignee: Martin R&F Inc., Montreal, Canada

[21] Appl. No.: 591,898

[22] Filed: Jan. 25, 1996

Related U.S. Application Data

[63] Continuation of Ser. No. 402,777, Mar. 9, 1995, abandoned, which is a continuation of Ser. No. 997,720, Dec. 31, 1992, abandoned.

[51] Int. Cl.$^6$ .................. A61K 38/00; C07K 5/00; C07K 7/00
[52] U.S. Cl. .................. 530/402; 530/327; 530/328; 530/329
[58] Field of Search .................. 530/327, 328, 530/329, 402; 514/14, 15, 16, 17

[56] References Cited

PUBLICATIONS

Faure et al., Binding and Internalization of Neurotensin in Hybrid Cells Derived from Septal Cholinergic Neurons, *Chemical Abstracts*, vol. 118, No. 13., 1993, Abst No: 117032h.
Carraway, R. & Leeman, S.E., The J. of Biol. Chem., 1973, 248:6854–6861.
Tanaka, Masu, and Nakanishi, Neuron, 1990, 4:947–854.
Hazum E., Chang K–J, & Cuatrecas P., Proc. of Natl. Acad. Sciences USA, 1979, 77:3038–3041.
Taylor D.L. & Wang Yu–Li, Nature, 1980, 284:405–410.
Schaffner et al., The J. of Neuroscience, 1987, 7:3088–3104.
Sadoul J.L. et al., Biochem. and Biophys. Res. Comm., 1984, 120(1):206–213.
Hammond et al., Science, Dec. 1986, 234:1237–1240.

*Primary Examiner*—Avis M. Davenport
*Attorney, Agent, or Firm*—Clark & Elbing LLP

[57] ABSTRACT

The present invention relates to compound having the formula:

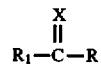

or a pharmaceutically acceptable acid salt thereof, wherein
R is a polypeptide moiety comprises an amino acid sequence:
-Y-Arg-Pro-Z-Ile-Leu;
wherein Y is Arg, and
Z is Tyr or Trp;
$R_1$ is a fluorophore selected from the group consisting of fluorescein, rhodamine, Blue fluorescent and Texas red; and
X is oxygen or sulfur. The present invention also relates to a method for the labeling of neurotensin receptors on cell surface and a method to isolate neurotensin-receptor expressing cells.

6 Claims, 6 Drawing Sheets

MARKER FOR NEUROTENSIN RECEPTOR

This application is a continuation of U.S. Ser. No. 08/402,777, filed Mar. 9, 1995 now abandoned, which is a continuation of U.S. Ser. No. 07/997,720, filed Dec. 31, 1992 now abandoned.

BACKGROUND OF THE INVENTION a) Field of the Invention

The invention relates to a selective fluorescent peptidic probe for neurotensin receptors, a method for in vitro labeling of neurotensin receptors on cell surface and a method to isolate neurotensin-receptor expressing cells.

b) Description of Prior Art

Neurotensin (NT) is a peptide of 13 amino acids (pGlu-Leu-Tyr-Glu-Asn-Lys-Pro-Arg-Arg-Pro-Tyr-Ile-Leu-OH) isolated from the hypothalamus (Carraway, R. & Leeman, S. E., The J. of Biol Chem., 1973, 248:6854–6861) and subsequently identified in the central nervous system (CNS) and the gastrointestinal tract of all vertebrates. Neurotensin fulfills a dual function as a neuromodulator in the nervous system and as a hormone in the gastrointestinal tract. Both modes of action imply as a first step the selective association of the neuropeptide with a specific receptor located on the plasma membrane of target cells.

Neurotensin-binding sites have been localized and characterized in various tissue preparations and in cell cultures from central and peripheral nervous systems. Pharmacological studies have demonstrated the existence of two populations of neurotensin binding sites: a low affinity and high capacity binding component (NTR1), from which neurotensin binding is displaced by the potent histamine antagonist, levocabastine; and a high affinity and low capacity binding components (NTR2) corresponding to the physiologically relevant form of the receptor. Both rat and human NTR2 components have been cloned and sequenced (Tanaka, Masu, and Nakanishi, Neuron, 1990, 4:947–854). Some of the biochemical events mediating neurotensin signal transduction have also been characterized.

In recent years, fluoro-labeled probes have been developed for localizing peptide, cytokine, drug, and hormone receptors at the cellular level in tissue and cell cultures (Hazum E., Chang K-J, & Cuatrecas P., Proc. of Natl. Acad. Sciences USA, 1979, 77:3038–3041). This concept, which involves labeling purified molecules covalently with fluorochromes such as fluorescein, has permitted the characterization of the kinetics, the distribution and the ultimate fate of many ligands in living cells (Taylor D. L. & Wang YuLi, Nature, 1980, 284:405–410).

It would be highly desirable to be provided with a non-toxic highly sensitive tool for biochemical, pharmacological and anatomical studies of the neurotensin receptor in both brain and peripheral tissues.

All markers for neurotensin receptors derived to date are of radioactive nature and hence have a limited half-life. In addition, radioactive probes for neurotensin receptors are costly and provide only static information on underlying biological processes.

Further, it would be highly desirable to be provided with a marker for neurotensin receptor which would allow for the isolation of neurotensin-receptor expressing cells. This application is of particular interest in view of the demonstration of a selective association of neurotensin receptors with midbrain dopaminergic cells and with basal forebrain cholinergic cells (Neurobiology of neurotensin, Kitagi and Nemerof eds., Proc. New York Acad. Sciences, 1992). Thus the isolation of neurotensin-receptor expressing cells would make it possible to sort out and selectively administer dopaminergic or cholinergic cells in diseases such as Parkinson's and Alzheimer's disease, respectively. The treatment of these diseases would be greatly improved if the population of cells administered were homogenous, since dissociated embryonic central nervous system preparations may contain cells that may otherwise interfere with the treatment.

Embryonic mouse and rat motoneurons have been isolated by Schaffner et al. using flow cytometry (The J. of Neuroscience, 1987, 7:3088–3104). These isolated cells were found to be 80% pure with respect to the presence of fluorescent label in cells examined with fluorescent microscopy immediately after sorting. These results suggest that isolated neurons from human embryonic tissue may be administered to patients in need of brain grafts.

It would be also highly desirable to be provided with a marker for neurotensin receptor which allows for receptor physiological studies in tissue slices and in cell cultures and for distinguishing cell surface from intracellular receptor components.

SUMMARY OF THE INVENTION

One aim of the present invention is to provide for a non-toxic highly sensitive and selective marker of the neurotensin receptor for biochemical, pharmacological and anatomical studies of the said receptor in both brain and peripheral tissues.

Another aim of the present invention is to provide for a marker of neurotensin receptors which would allow for the isolation of neurotensin-receptor expressing cells.

Another aim of the present invention is to provide for a marker of neurotensin receptors which allows for receptor physiological studies in vivo or in vitro and for distinguishing cell surface from intracellular receptor components.

In accordance with the present invention there is provided a compound having the formula:

or a pharmaceutically acceptable acid salt thereof, wherein

R is a polypeptide moiety comprising an amino acid sequence:

-Y-Arg-Pro-Z-Ile-Leu (SEQ ID NO:1);

wherein Y is Arg, and

Z is Tyr or Trp;

$R_1$ is a fluorophore selected from the group consisting of fluorescein, rhodamine, Blue fluorescent and Texas red; and X is oxygen or sulfur.

In accordance with the present invention there is provided for in vitro labeling of neurotensin receptors on cell surface, which comprises the steps of:

a) incubating dissociated cells, cell culture preparations or tissue slices with a compound of the present invention; and b) visualizing said compound of step a) using flow cytometry or epifluorescence/confocal microscopic methods.

In accordance with the present invention there is also provided a method to isolate neurotensin-receptor expressing cells, which comprises the steps of:

a) incubating dissociated cells or cell culture preparations with a compound of the present invention;

b) isolating cells bound to the compound of the present invention using flow cytometric cell-sorting methods; and c) injecting labeled sorted cells in live animals or in human patients.

In accordance with the present invention there is provided a method for the treatment of Parkinson, Alzheimer and/or others neurodegenerative diseases, which comprises administering to a patient neurotensin-receptor expressing cells isolated according to the method of the present invention.

DETAILED DESCRIPTION OF THE INVENTION

In the present invention the amino acids are identified by the conventional three-letter abbreviations as indicated below:

| | |
|---|---|
| Alanine | Ala |
| Arginine | Arg |
| Asparagine | Asn |
| Aspartic Acid | Asp |
| Cysteine | Cys |
| Glutamic Acid | Glu |
| Glycine | Gly |
| Histidine | His |
| Leucine | Leu |
| Lysine | Lys |
| Methionine | Met |
| Ornithine | Orn |
| Phenylalanine | Phe |
| Proline | Pro |
| Serine | Ser |
| Threonine | Thr |
| Tryptophane | Trp |
| Tyrosine | Tyr |
| D-Tyrosine | tyr |
| Valine | Val |

The present invention relates to highly sensitive fluorescent probes which allow for rapid and precise characterization of neurotensin receptor binding properties on whole cells.

The fluorescent compounds of the present invention have the following general formula:

$$R_1-\overset{\overset{\displaystyle X}{\|}}{C}-R.$$

R is a polypeptide moiety which consists essentially of an amino acid sequence selected from the group consisting of:

-continued

—Leu—tyr—Glu—Asn—Orn—Pro—Arg—Arg—Pro—Tyr—Ile—Leu;
—Leu—tyr—Glu—Asn—Orn—Pro—Arg—Arg—Pro—Trp—Ile—Leu;
—Glu$^1$—Leu—Tyr—Glu—Asn—Lys—Pro—Arg—Arg—Pro—Tyr—Ile—Leu;
—Glu—Leu—Tyr—Glu—Asn—Lys—Pro—Arg—Arg—Pro—Trp—Ile—Leu;
—Glu—Leu—Tyr—Glu—Asn—Orn—Pro—Arg—Arg—Pro—Tyr—Ile—Leu;
—Glu—Leu—Tyr—Glu—Asn—Orn—Pro—Arg—Arg—Pro—Trp—Ile—Leu;
—Glu—Leu—tyr—Glu—Asn—Lys—Pro—Arg—Arg—Pro—Tyr—Ile—Leu;
—Glu—Leu—tyr—Glu—Asn—Lys—Pro—Arg—Arg—Pro—Trp—Ile—Leu;
—Glu—Leu—tyr—Glu—Asn—Orn—Pro—Arg—Arg—Pro—Tyr—Ile—Leu;
—Glu—Leu—tyr—Glu—Asn—Orn—Pro—Arg—Arg—Pro—Trp—Ile—Leu;
—pGlu—Leu—Tyr—Glu—Asn—Lys—Pro—Arg—Arg—Pro—Tyr—Ile—Leu;
—pGlu—Leu—Tyr—Glu—Asn—Lys—Pro—Arg—Arg—Pro—Trp—Ile—Leu;
—pGlu—Leu—Tyr—Glu—Asn—Orn—Pro—Arg—Arg—Pro—Tyr—Ile—Leu;
—pGlu—Leu—Tyr—Glu—Asn—Orn—Pro—Arg—Arg—Pro—Trp—Ile—Leu;
—pGlu—Leu—tyr—Glu—Asn—Lys—Pro—Arg—Arg—Pro—Tyr—Ile—Leu;
—pGlu—Leu—tyr—Glu—Asn—Lys—Pro—Arg—Arg—Pro—Trp—Ile—Leu;
—pGlu—Leu—tyr—Glu—Asn—Orn—Pro—Arg—Arg—Pro—Tyr—Ile—Leu; and
—pGlu—Leu—tyr—Glu—Asn—Orn—Pro—Arg—Arg—Pro—Trp—Ile—Leu.

In accordance with the present invention, each of the amino acid residues identified at positions 1 to 8 may be substituted by Lys or Orn.

Further, the amino acid sequence of the polypeptide moiety in accordance with the present invention may be lengthened at the N- or C-terminal as long as the neurotensin-like biological activity is preserved.

In accordance with the present invention, the expression neurotensin-like biological activity is intended to mean that the polypeptide induces biological effects similar to those of neurotensin and/or binds with high affinity and selectivity to the neurotensin receptor.

$R_1$ is a fluorophore moiety selected from the group consisting of fluorescein, such as fluorescein isothiocyanate, 5-carboxy-fluorescein, 6-carboxy-fluorescein, rhodamine, such as tetramethyl rhodamine isiothiocyanate, Blue fluorescent, such as BODIPY™, and Texas red.

In accordance with the present invention, other fluorophores may be used where neurotensin-like biological activity is preserved.

In accordance with the present invention, the fluorophores may be linked to the polypeptide moiety at position ranging from 1 to 8 via a thiocarbamyl bond, where X is sulfur, or a peptide bond, where X is oxygen.

Figure 1:
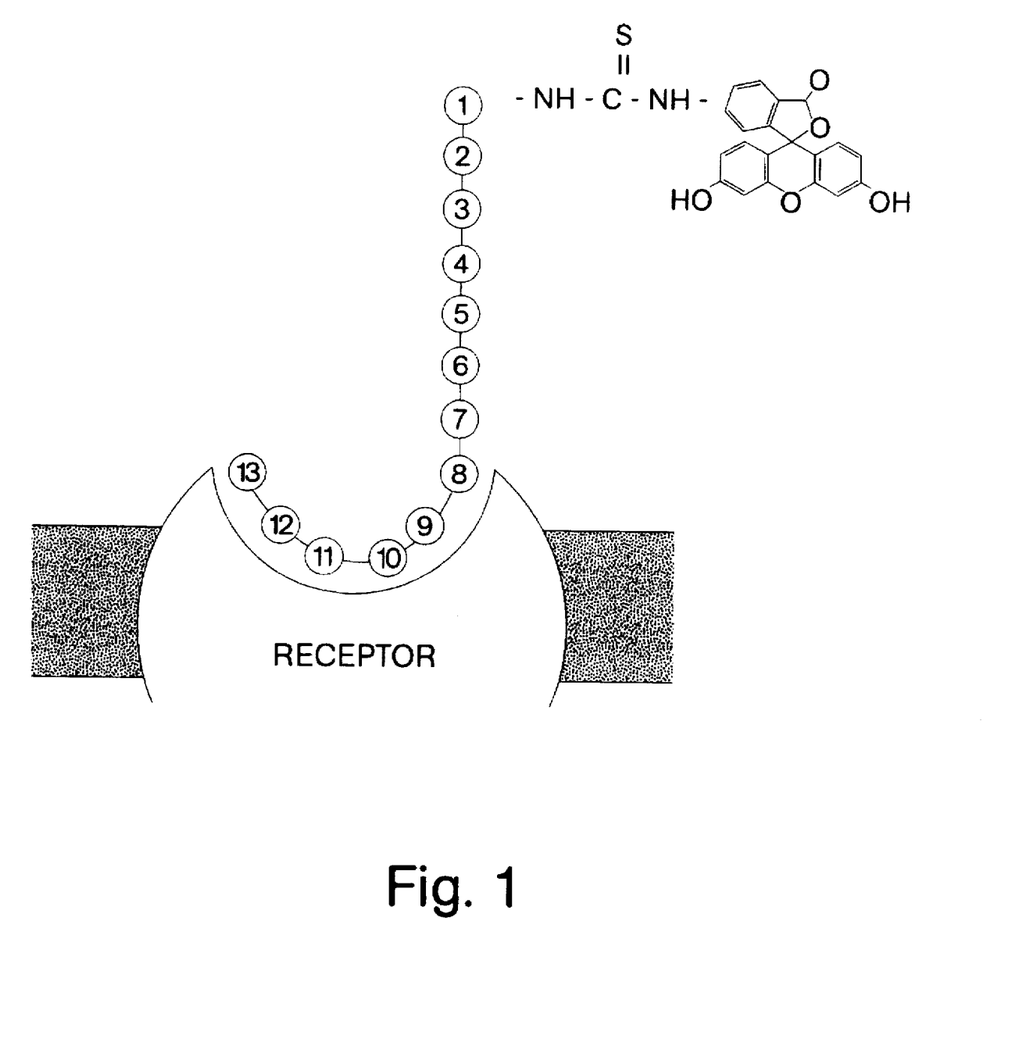
FIG. 1 is the structure of N-fluoresceyl thiocarbamyl-[Glu$^1$] neurotensin, in accordance with one embodiment of the present invention.

The preferred compound in accordance with the present invention is N-fluoresceyl thiocarbamyl-[Glu$^1$] neurotensin (N-FTC-[Glu$^1$]NT) as shown in FIG. 1.

Although there have been previous attempts at conjugating peptides with fluorescein, N-FTC-[Glu$^1$]NT is the first example of a successful conjugation of fluorescein with the tridecapeptide neurotensin. The salient features of one compound of the present invention are:

(1) the selective attachment of the fluorescein molecule to the neurotensin N-terminus;

(2) the purification of the conjugated compound to approximately 99% purity allowing for optimal detection sensitivity;

(3) the similarity of its pharmacological properties with those of the native peptide; and (4) the fact that it is 100% non-toxic and has a demonstrated shelf life of at least one year.

The fluorescent peptide compounds of the present invention offer a new, inexpensive and highly sensitive tool for biochemical, pharmacological and anatomical studies of the neurotensin receptor in both brain and peripheral tissues. The present fluorescent probes offer several advantages over the use of radioactive compounds.

The compounds of the present invention do not have any of the common drawbacks of radioactive molecules such as short half-life, high cost and slow detection yield (which may imply weeks of photographic exposure). Further, they compensate for two major shortcomings of current neurotensin radioactive probes: their low specific activity (which admittedly is higher with iodinated than tritiated ligands, but also entails greater biohazards) and the fact that they essentially provide static information (i.e. information that is not applicable to studying living processes in real time).

In addition to providing a non-radioactive approach to the characterization of neurotensin receptors, the fluorescent compounds of the present invention may be used for a number of additional applications unsuited to radioactive probes. These include the following:

(1) these fluorescent compounds may be readily applied to the isolation of neurotensin-receptor expressing cells, using flow cytometric cell-sorting methods. Similarly, receptor binding studies may be carried out on whole cells by flow cytometry.

(2) The fluorescent compounds of the present invention may be used for real time visualization of physiological processes (receptor aggregation, capping and internalization) using confocal laser microscopy on brain slices or in cell culture preparation. The same technique may be used for distinguishing cell surface with respect to intracellular components.

(3) Confocal microscopic visualization of the bound fluorescent compounds may be combined with that of other cell markers (e.g. Biocytin™, Lucifer™ yellow) for identification of neurotensin receptors on electrophysiologically recorded cells. It may also be conjugated to the immunocytochemical characterization of the cells and/or compartments harboring the labeled receptors, using appropriate fluorescent-tagged antibodies.

In accordance with one embodiment of the present invention, N-FTC-[Glu$^1$]NT is prepared according to the following procedure.

1-Fluorescent labeling of neurotensin

Figure 3:
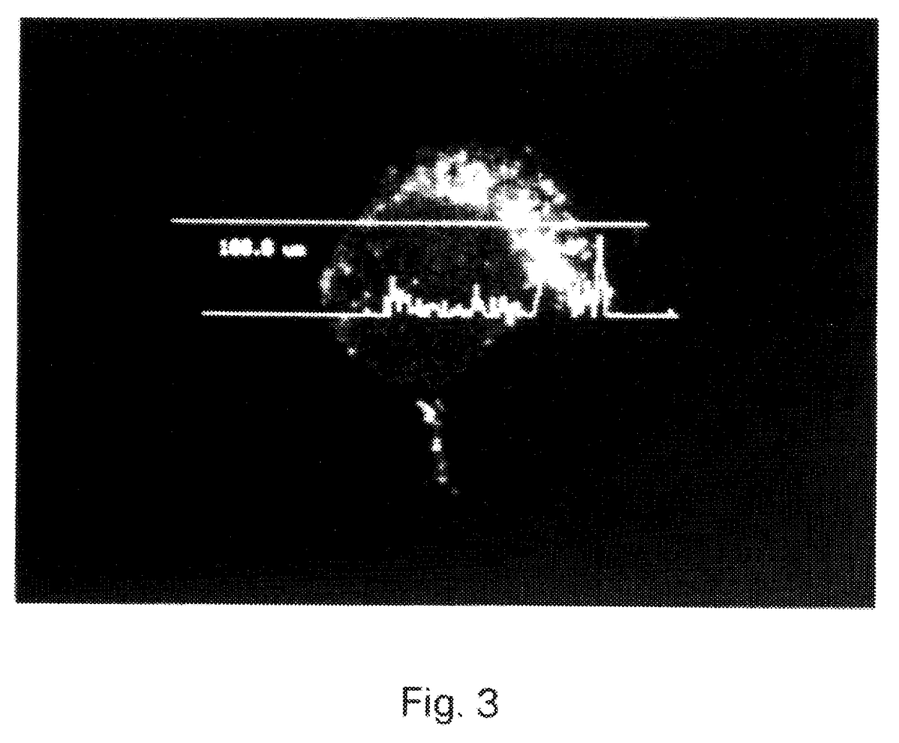
FIG. 3 is a confocal optical section of a cholinergic/hybrid (SN6) cell incubated with a compound of the present invention.

[Glu$^1$]NT was synthesized by solid phase technique using a scheme based on t-Boc chemistry/acid labile amino acid protecting groups. After deprotection of the last N-amino group, acylation was performed by fluorescein isothiocyanate (FITC, Sigma, 6-fold excess) in anhydrous dimethylformamide (DMF) containing 5% N,N-diisopropylethylamine (DIEA) for 2 hours at room temperature with stirring. Completion of the coupling was ascertained by a ninhydrin colorimetric test. The acyl-peptide-resin intermediate was then extensively washed with DMF and dried in vacuo. It was submitted to hydrogen fluoride cleavage to deprotect amino acid side chains and to cleave the fluorescein thiocarbamyl (FTC) peptide from the resin. The FTC-peptide was solubilized in trifluoroacetic acid (TFA) and subjected to rotary evaporation in vacuo. It was then purified by preparative high pressure liquid chromatography (HPLC) on a parsil 10 ODS-3 Whatman™ column (10-um particle size; 2.2 cm×50 cm), using a binary solvent system consisting of 0.01% aqueous TFA, pH 2.9 and acetonitrile ($CH_3CN$)- 0.01% TFA and an appropriate gradient. Elution of the peptide was monitored at 214 nm. Collected fractions were readily screened by analytical HPLC using both UV and fluorescence detection (excitation, 338 nm; emission, 425 nm), pooled accordingly, evaporated in vacuo to remove $CH_3CN$ and lyophilized twice. The purified N-FTC[$Glu^1$] NT was analyzed for homogeneity by analytical HPLC on a u Bondapak™ $C_{18}$ column (10-um particle; 0.39 cm×15 cm) using appropriate linear gradients of 0.01% aqueous TFA, pH 2.9 and 0.01% TFA-$CH_3CN$ and 0.01M ammonium acetate and $CH_3CN$ (FIG. 3, where the position of [$Glu^1$]NT and its fluorescent analog FTC[$Glu^1$]NT are indicated on the profiles). Its amino acid composition was assessed by quantitative amino acid analysis after acidic hydrolysis in vacuo (6N HCl, 110° C., 18 h) and carboxypeptidase Y (CPY) digestion (6 U/0.3 umole, 37° C., 48 h).

Figure 2:
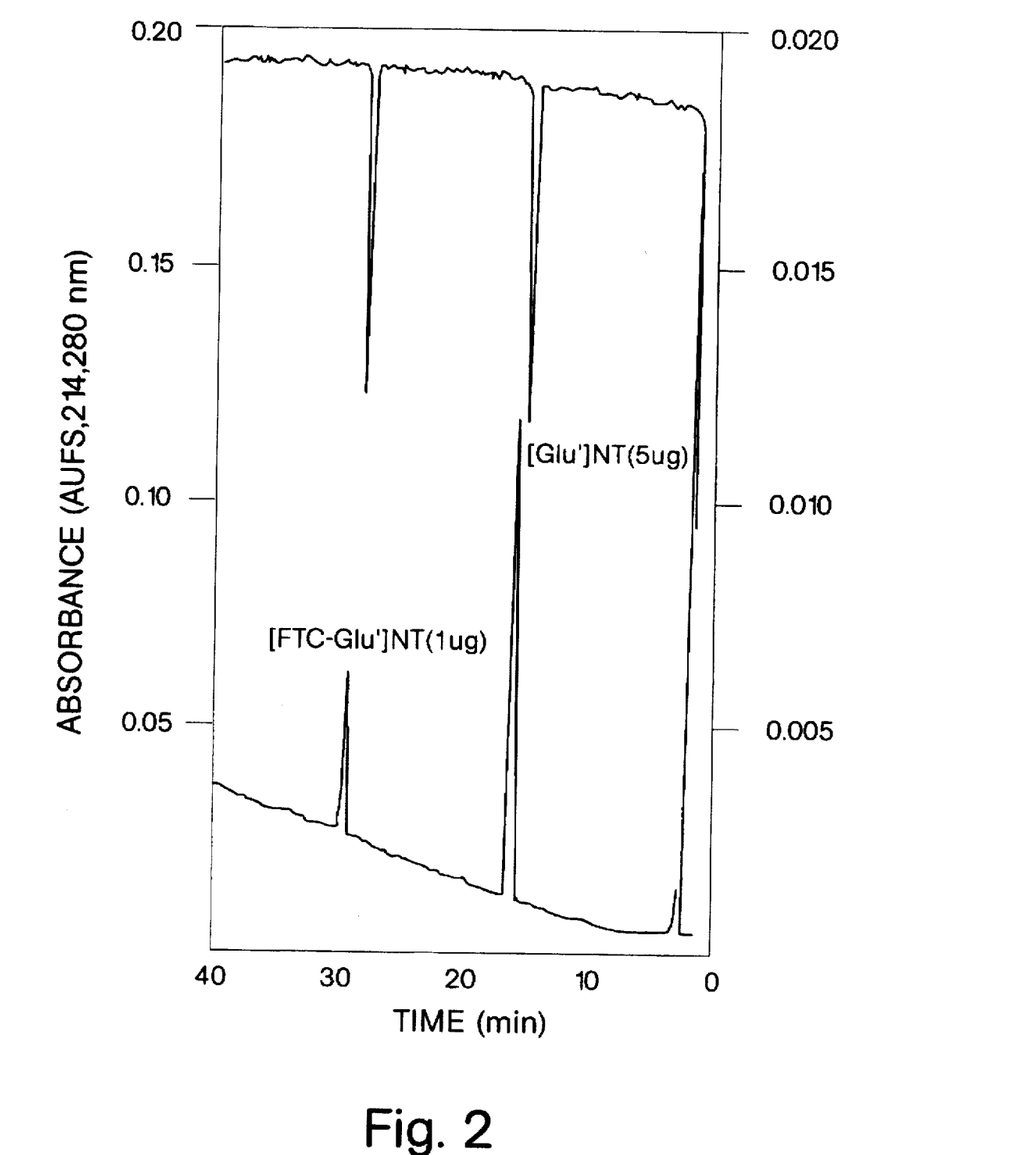
FIG. 2 is an analytical chromatographic profile of a compound of the present invention and of neurotensin.

The site of attachment of the fluorosceyl derivative molecule to the neurotensin N-terminus was identified as $N\alpha$-$Glu^1$. The structure of the fluorescent peptide was confirmed by mass spectral analysis. The degree of homogeneity was determined by U.V. and fluorescence detection to 99%. The modification of semi-protected neurotensin with FITC yielded a selective incorporation of one mole FITC/mole unprotected peptide. N-FTC-[$Glu^1$]NT was evaluated to be pure as indicated by a single elution peak from reverse-phase HPLC allowing for optimal detection sensitivity (FIG. 2). The molecular weight of N-FTC-[$Glu^1$]NT is 2080. The coumpound is freely soluble in distilled water or aqueous buffer, and is stable if protected from light and maintained at 4° C. Finally, FTC-NT is 100% non-toxic.

2-Competitive binding assay

Figure 4:
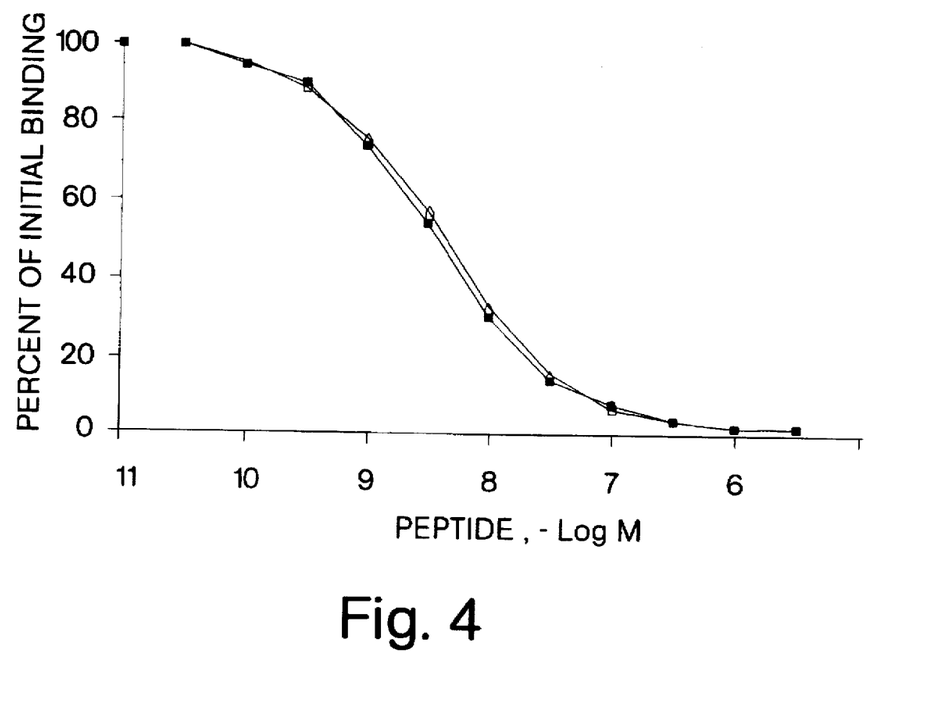
FIG. 4 is a displacement curve of the binding of a compound of the present invention on mouse brain membranes by iodinated-neurotensin.

The binding of monoiodo $^{125}I$-$Tyr_3$-neurotensin was performed on purified brain membranes from adult male mice as described previously (Sadoul J. L. et al., Biochem. and Biophys. Res. Comm., 1984, 120(1):206–213). Briefly, membranes were incubated with 0.1 nM of radiolabeled peptide in the presence of varying concentrations of N-FTC-[$Glu^1$]NT in 50 mM Tris HCl pH 7.5 containing 0.2% bovine serum albumin and 1 mM 1,10-phenanthroline. The reaction was carried out for 20 minutes at 22° C. and stopped by the addition of 2 ml ice-cold buffer. Membranes were then subjected to immediate filtration over Gelman™-filters (Millipore™) under vacuum using a Millipore™ filtration apparatus. They were then thoroughly washed and their radioactivity content was measured in a gamma counter. The data were expressed as the percentage of specific binding of the radioligand in the absence of competitor. $IC_{50}$ values were obtained graphically and then corrected for the occupancy by the labeled ligand to obtain $K_i$ values. The $K_i$ values presented are the geometric mean [anti-log of averaged log ($K_i$) values]±SEM. The data were analyzed on an IBM/XT microcomputer using EBDA/LIGANG programs. As can be seen in FIG. 4, the fluorescent analogue completely displaces specific $^{125}I$-$Tyr_3$-neurotensin binding in a dose dependent manner. Scatchard analysis of the data indicates that the binding is virtually the same as that of native neurotensin with an $IC_{50}$ of 0.55 nM and a pseudo-Hill coefficient of approximately 1.

EXAMPLE I

In vitro labeling of neurotensin receptors on Rat brain tissue sections

Rats were sacrificed by decapitation, the brains were rapidly removed, blocked in the coronal plane and frozen at −40° C. 25 μm-thick frozen sections of the substantia nigra were cut on a cryostat and incubated with $10^{-4}$–$10^{-6}$M fluoro-neurotensin diluted in binding buffer (pH 7.4). The incubations were performed at 4° C. in the dark for 60 minutes to allow for equilibration, after which the sections were rapidly rinsed in phosphate-buffered-saline (4×60 seconds each), dipped in double-distilled water, and air dried under a cool stream of air. The distribution of the fluorescent labeling was examined under a Leica Diaplan™ microscope using a high pressure 100-W mercury lamp and the appropriate dichroic filter combinations for excitation/emission of fluorescein (485/520 nm).

Controls for these experiments included: (1) examination of sections incubated in the absence of the fluorescent ligand to determine background autofluorescence, and in the presence of a 1000-fold excess of unlabeled ligand for the determination of the non-specific binding; and (2) examination of regions of the nervous system known to be devoid of neurotensin receptors.

Figure 5A:
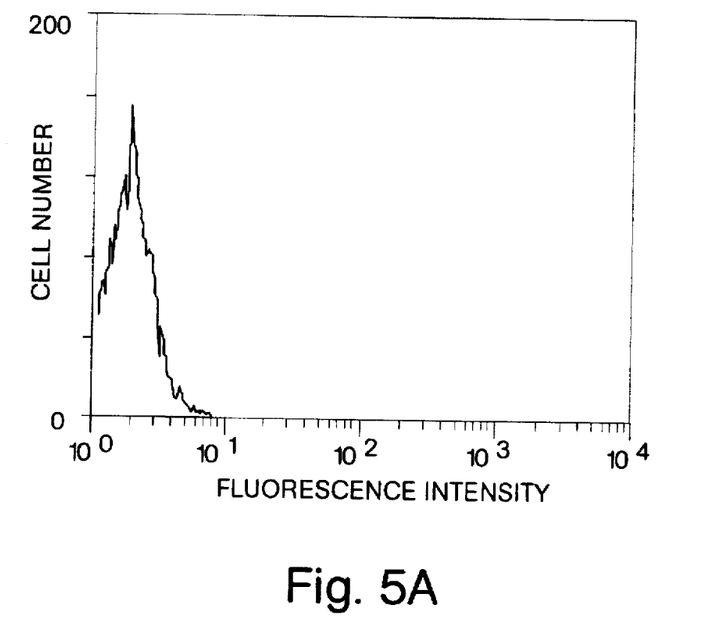
FIG. 5 is a light microscopic image of fluoro-neurotensin labeling of dopaminergic neurons in rat brain sections.
Figure 5B:
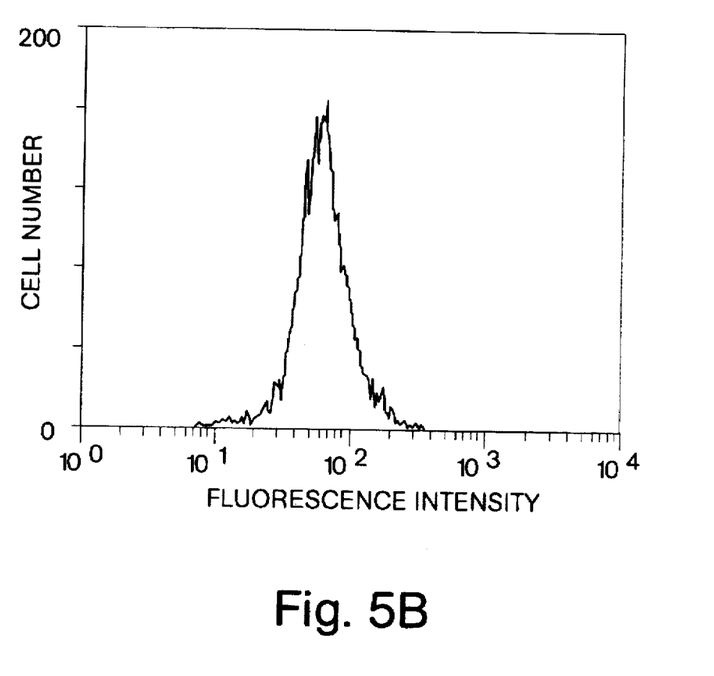

The anatomical distribution of specifically bound fluorescent ligand in the ventral midbrain tegmentum is illustrated in FIG. 5.

In the substantia nigra pars compacta the label is seen to be selectively accumulated over nerve cell bodies and proximal dendrites. The labeled neurons are ovoid and fusiform in shape with their long axis oriented parallel to the dorsal surface of the pars reticulata. In the latter, the label is mainly confined to a few scattered perikaria, however several labeled processes are seen to radiate from the cells in the pars compacta.

In the ventral tegmental area, the labeling is intense and associated with both nerve cell bodies and surrounding neuropil. In the parabrachial pigmentous division, the labeling is interrupted by areas devoid of label corresponding to the trans-tegmental fiber bundles. The fluorescent labeling was no longer apparent in sections incubated with an excess of unlabeled neurotensin. No autofluorescence was observed except a few orange spots in some cells, typical of lipofuscin aggregates.

EXAMPLE II

Flow cytometric analysis of fluoro-neurotensin binding to cholinergic hybrids cells Hybridomas cells (SN6) were produced by the fusion of embryonic septal cells with murine neuroblastoma and generously provided by Hammond et al. (Science, December 1986, 234:1237–1240). SN cells were grown in petri dishes (100 $mm^2$) in Dubelcco's modified Eagle's medium (DMEM) containing 44 mM $NaHCO_3$ and 10% fetal calf serum (Gibco BRL) in a humidified atmosphere of 90% air, 10% $CO_2$ at 37° C.

For flow cytometry, the cells (1×$10^6$ cell/0.1 ml) were washed in PBS and incubated with various concentrations of fluoro-neurotensin in Hepes-Tris-buffer, pH 7.4, in the presence (non-specific) or the absence (total binding) of a 100-fold excess of unlabeled neurotensin. After incubation at 40° C. or 20° C. for 1 hour, the cells were washed and analyzed with a Becton-Dickinson™ Facscan flow cytometer and consort 30 software.

Figure 6:
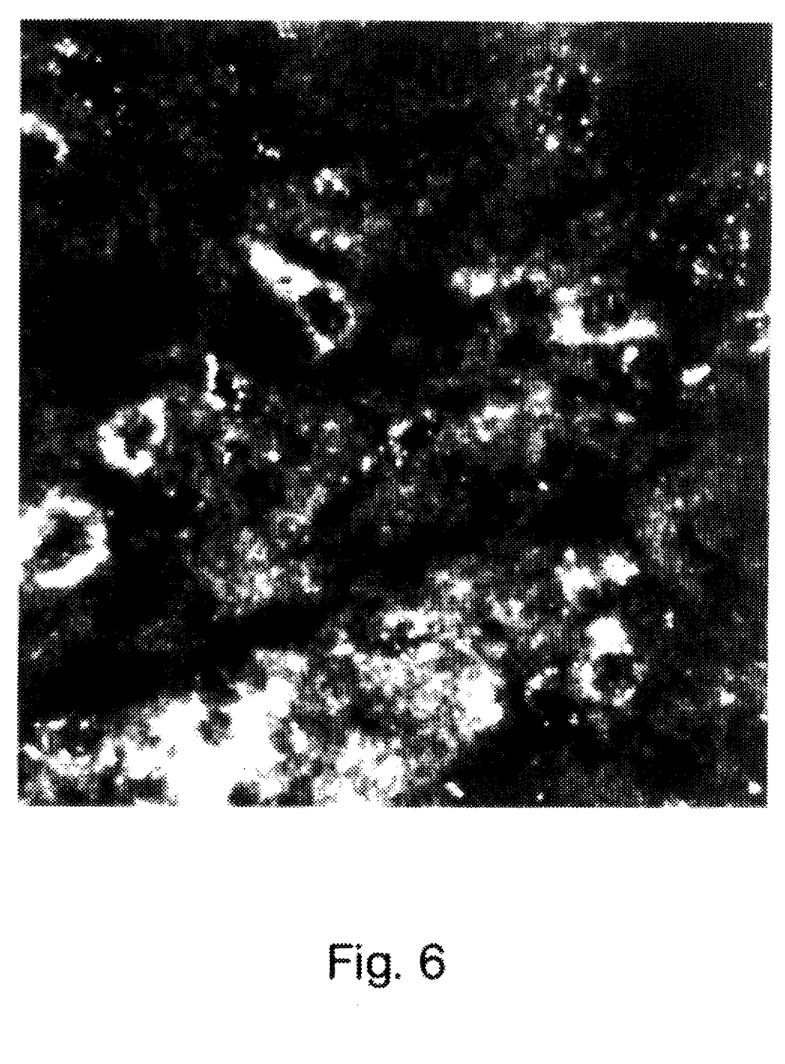
FIG. 6 is a flow cytometric histogram of N-fluorescein isothiocarbamyl-[Glu$^1$] neurotensin binding on SN6 cholinergic hybrid cells at 4° C. in the presence (a) and in the absence (b) of non-fluorescent neurotensin.

Flow cytometric histograms of N-FTC-[$Glu^1$]NT binding to SN6 cholinergic hybrid cells are illustrated in FIG. 6. The majority (97.4%) of the cells displayed specific fluoro-neurotensin binding at both 4° C. and 20° C. Saturation of the binding was both time and temperature dependent. Maximal binding densities were higher at 4° C. than at 20° C., presumably reflecting a down regulation of cell surface receptors subsequent to internalization.

EXAMPLE III

Confocal microscopic visualization of neurotensin binding sites on cholinergic hybrid cells.

SN6 cholinergic hybrid cells were incubated with N-FTC-[Glu$^1$]NT, under the same conditions as above and the distribution of bound fluorescent molecules was analyzed by confocal microscopy.

Confocal imaging was performed with a Leica™ confocal laser scanning microscope configured with a Leica Diaplan™ inverted microscope (equipped with a 40×NPL oil immersion fluotar objective of 1.30 numerical aperture), an argon ion laser (488 nm) with an output power of 2-50 mW, and a VME bus with an MC 68020/68881™ computer system integrated to an optical disc for image storage. All image generating and processing operations were performed on a Leica™ confocal laser microscope software. Optical scanning images (512×512 pixels) of cultured cells were made at 0.1 μm intervals for a total of 26 sections per scanning sequence. From this data volume, a single composite image of each cell was generated using extended focus image construction.

Confocal laser microscopic examination of cells incubated with fluoro-neurotensin at 4° C. showed prominent staining of the cell borders, suggesting confinement of the label to the cell membrane. Upon warming of these cells up to 37° C. for 10 minutes, the surface fluorescence intensity diminished and multiple small, bright fluorescent particles appeared in the cytoplasm. After 30 min at 37° C., these fluorescent endosome-like elements accumulated and formed a perinuclear ring as illustrated in FIG. 2.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

We claim:

1. A compound having a formula:

or a pharmaceutically acceptable acid salt thereof, wherein
R is a polypeptide moiety having 13 or fewer amino acid residues, and comprising an amino acid sequence:

-Y-Arg-Pro-Z-Ile-Leu; (SEQ ID NO.:1)

wherein Y is selected from the group consisting of Arg, Pro-Arg, A-Pro-Arg, Asn-A-Pro-Arg, Glu-Asn-A-Pro-Arg, B-Glu-Asn-A-Pro-Arg, Leu-B-Glu-Asn-A-Pro-Arg or W-Leu-B-Glu-Asn-A-Pro-Arg wherein, A is Lys or Orn;
B is Tyr or tyr;
W is Glu or pGlu; (SEQ ID NO:2) and
Z is Tyr or Trp;

$R_1$ is a light-emitting fluorophore; and

X is oxygen or sulfur;

wherein $R_1$ is linked to R via an Nα-amino group of an amino-terminal amino acid residue of Y and wherein said amino acid residue is selected from the group consisting of W, Leu, B, Glu, Asn, Pro, Lys, or Orn.

2. A compound according to claim 1, wherein said polypeptide R is neurotensin or an analog thereof.

3. A compound according to claim 1, wherein R is Glu-Leu-Tyr-Glu-Asn-Lys-Pro-Arg-Arg-Pro-Tyr-Ile-Leu, is fluorescein thiocarbamyl and R is linked via its N-terminus.

4. A compound having the formula:

or a pharmaceutically acceptable acid salt thereof, wherein

R is a polypeptide moiety having 13 or fewer amino acid residues, and comprising the amino acid residues 8-13 of neurotensin, $R_1$ is a fluorophore selected from the group consisting of fluoroscein, rhodamine, Blue fluorescent and Texas red; and X is oxygen or sulfur.

5. A compound according to claim 1, wherein said fluorophore is selected from the group consisting of fluorescein, rhodamine, Blue fluorescent, and Texas red.

6. A compound according to claim 1, wherein said compound is at least 99% homogeneous.

* * * * *

UNITED STATES PATENT AND TRADEMARK OFFICE
CERTIFICATE OF CORRECTION

PATENT NO. : 5,760,188
DATED : June 2, 1998
INVENTOR(S) : Alain Beaudet, Marie-Pierre Faure, and Pierrette Gaudreau It is certified that error appears in the above-identified patent and that said Letters Patent is hereby corrected as shown below:

On the cover page, item [73], under Assignee, replace "Martin R&F Inc." with --Martinex R&D Inc.--.

Signed and Sealed this

Eighth Day of September, 1998

Attest:

BRUCE LEHMAN

Attesting Officer

Commissioner of Patents and Trademarks